United States Patent [19]

Yu

[11] 4,185,021
[45] Jan. 22, 1980

[54] 5-(P-NITROPHENYL)-2-FURALDEHYDE 2-(2-HYDROXYETHYL)HYDRAZONE

[75] Inventor: Chia-Nien Yu, Norwich, N.Y.

[73] Assignee: Morton-Norwich Products, Inc., Norwich, N.Y.

[21] Appl. No.: 11,208

[22] Filed: Feb. 12, 1979

[51] Int. Cl.$^2$ ............................................ C07D 307/52
[52] U.S. Cl. ................................. 260/347.7; 424/285
[58] Field of Search ........................................ 260/347.7

[56] References Cited

U.S. PATENT DOCUMENTS

| 4,066,672 | 1/1978 | Pelosi ................................. 260/347.7 |
| 4,070,380 | 1/1978 | Pelosi et al. ........................ 260/347.7 |

*Primary Examiner*—Richard Raymond
*Attorney, Agent, or Firm*—Anthony J. Franze

[57] ABSTRACT

5-(p-Nitrophenyl)-2-furaldehyde 2-(2-hydroxyethyl)hydrazone is useful as an anti-inflammatory.

1 Claim, No Drawings

5-(P-NITROPHENYL)-2-FURALDEHYDE 2-(2-HYDROXYETHYL)HYDRAZONE

This invention is concerned with the compound 5-(p-nitrophenyl)-2-furaldehyde 2-(2-hydroxyethyl)hydrazone. This compound possesses pharmacologic activity. It is particularly useful as an anti-inflammatory agent as evidenced by its ability to inhibit edema induced in rats by the administration of carrageenin. Thus, when administered at a dose of 300 mg/kg suspended in a vehicle such as aqueous methyl cellulose per os to rats receiving carageenin, edema associated with that substance is inhibited [Winter et al., P.S.E.B.M. 111:544].

The compound of this invention is readily composed in a variety of administrable forms such as tablets, suspensions, capsules and the like employing conventional vehicles and adjuvants with which there is no incompatibility.

The compound of this invention is currently prepared in accordance with the following description:

A mixture of 87 g (0.4 mole) of 5-(p-nitrophenyl)-2furancarboxaldehyde and 48 g (0.63 mole) of 2-hydroxyethylhydrazine in 2200 ml of ethanol was heated on a steam bath with stirring for ¾ hour. After cooling, the red crystalline solid was filtered, washed well with alcohol and air-dried. The yield was 75 g (72%), m.p. 129°–131°.

Recrystallization from ethanol gave m.p. 135°–136°.

Anal. Calcd. for $C_{13}H_{13}N_3O_4$: C, 56.72%; H, 4.76%; N, 15.27%. Found: C, 57.05%; H, 4.90%; N, 15.06%.

What is claimed is:

1. The compound 5-(p-nitrophenyl)-2-furaldehyde 2-(2-hydroxyethyl)-hydrazone.

* * * * *